US011559560B2

(12) United States Patent
Fairhead et al.

(10) Patent No.: US 11,559,560 B2
(45) Date of Patent: Jan. 24, 2023

(54) MODIFIED BACTERIOPHAGE

(71) Applicant: PHICO THERAPEUTICS LTD., Cambridge (GB)

(72) Inventors: Heather Fairhead, Histon (GB); Adam Wilkinson, Chrishall (GB); Sarah Holme, Royston (GB); Katy Pitts, Royston (GB); Alison Jackson, Lauder (GB)

(73) Assignee: PHICO THERAPEUTICS LTD., Cambridge (GB)

( * ) Notice: Subject to any disclaimer, the term of this patent is extended or adjusted under 35 U.S.C. 154(b) by 487 days.

(21) Appl. No.: 16/128,558

(22) Filed: Sep. 12, 2018

(65) Prior Publication Data

US 2019/0071648 A1 Mar. 7, 2019

Related U.S. Application Data

(62) Division of application No. 15/147,483, filed on May 5, 2016, now Pat. No. 10,106,784, which is a division of application No. 14/190,727, filed on Feb. 26, 2014, now Pat. No. 9,359,596, which is a division of application No. 12/672,311, filed as application No. PCT/EP2008/060360 on Aug. 6, 2008, now Pat. No. 8,697,049.

(30) Foreign Application Priority Data

Aug. 7, 2007 (GB) ..................................... 0715416

(51) Int. Cl.

*C12N 7/00* (2006.01)
*A61K 38/16* (2006.01)
*C07K 14/32* (2006.01)
*A61K 9/00* (2006.01)

(52) U.S. Cl.

CPC .......... *A61K 38/164* (2013.01); *A61K 9/0014* (2013.01); *A61K 9/0053* (2013.01); *C07K 14/32* (2013.01); *C12N 7/00* (2013.01); *C12N 2795/00032* (2013.01); *C12N 2795/00043* (2013.01)

(58) Field of Classification Search

None
See application file for complete search history.

(56) References Cited

U.S. PATENT DOCUMENTS 7,632,512 B2 12/2009 Fairhead et al.
7,968,699 B2 6/2011 Haefner et al.
8,133,498 B2 3/2012 Fairhead
8,691,542 B2 * 4/2014 Guilak .................. A61K 35/28 435/180
8,697,049 B2 4/2014 Fairhead et al.
9,359,596 B2 6/2016 Fairhead et al.
2004/0097705 A1 5/2004 Fairhead
2008/0268502 A1 10/2008 Haefner et al.
2010/0239536 A1 9/2010 Fairhead et al.
2014/0242032 A1 8/2014 Fairhead et al.

FOREIGN PATENT DOCUMENTS

WO 2002/040678 5/2002
WO 2004/113375 12/2004

OTHER PUBLICATIONS

Wong et al. A Potential Food-Grade Cloning Vector for *Streptococcus thermophilus* That Uses Cadmium Resistance as the Selectable Marker Applied and Environmental Microbiology, Oct. 2003, p. 5767-5771.*
Novick, R. P. 1991. Genetic systems in staphylococci. Methods Enzymol. 204:587-636.*
Lysogenic cycle—Wikipedia p. 1 of 5; downloaded Oct. 30, 2021.*
"The New Shorter Oxford English Dictionary On Historical Principles," Clarenden Press, Oxford, vol. 1, p. 489, 2002.
Bacteriophage From Wikipedia, the free encyclopedia last visited Mar. 4, 2015.
Barnard et al., "SASP: rapid bactericidal activity against USA strains of meticillin-resistant *Staphylococcus aureus*," Clinical Microbiology and Infection, vol. 14, No. s7, Apr. 2008, pp. s131-s132, XP002505321.
Bowker et al., "SASP: Kill Kinetics against Diverse Antibiotic Resistant *Staphylococcus aureus*," (Abstract), 47th Interscience Conference on Antimicrobial Agents and Chemotherapy, Chicago, IL, Sep. 20, 2007.
Doherty et al. "Functional Analysis of luxS in *Staphylococcus aureus* Reveals a Role in Metabolism but Not Quorum Sensing," J. Bacteriol. Apr. 2006 vol. 188 no. 8 2885-2897.
Forsyth et al., "A genome-wide strategy for the identification of essential genes in *Staphylococcus aureus*," Molecular Microbiology (2002) 43(6), 1387-1400.
Forsyth et al., "A genome-wide strategy for the identification of essential genes in *Staphylococcus aureus*," Molecular Microbiology, vol. 43, Issue 6, pp. 1387-1400, Mar. 2002.
Francesconi et al., "Immunoelectron microscopic localization of small, acid-soluble spore proteins in sporulating cells of Bacillus subtillis," J. Bacteriol. Dec. 1988 vol. 170 No. 12 5963-5967.
Frenkiel-Krispin et al., "Structure of the DNA-SspC Complex: Implications for DNA Packaging, Protection, and Repair in Bacterial Spores," J. Bacteriol. Jun. 2004 vol. 186 No. 11 3525-3530.
Gill et al., "Insights on Evolution of Virulence and Resistance from the Complete Genome Analysis of an Early Methicillin-Resistant *Staphylococcus aureus* Strain and a Biofilm-Producing Methicillin-Resistant *Staphylococcus epidermidis* Strain," J. Bacteriol. Apr. 2005 vol. 7 2426-2438.

(Continued)

*Primary Examiner* — Maria G Leavitt
(74) *Attorney, Agent, or Firm* — Robin L. Teskin; Baker, Donelson, Bearman, Caldwell & Berkowitz PC

(57) ABSTRACT

Provided is a modified bacteriophage capable of infecting a target bacterium, which bacteriophage includes an α/β small acid-soluble spore protein (SASP) gene encoding a SASP which is toxic to the target bacterium, wherein the SASP gene is under the control of a constitutive promoter which is foreign to the bacteriophage and the SASP gene.

20 Claims, 7 Drawing Sheets

Specification includes a Sequence Listing.

(56) References Cited

OTHER PUBLICATIONS

Hanlon, "Bacteriophages: an appraisal of their role in the treament of bacterial infections," International Journal of Antimicrobial Agents, vol. 30, Issue 2, Aug. 2007, pp. 118-128.

Kuroda et al., "Whole genome sequencing of meticillin-resistant *Staphylococcus aureus*," The Lancet, vol. 357, Issue 9264, Apr. 21, 2001, pp. 1225-1240.

Lambda phage from Wikipedia, the free encyclopedia 2013.

Lodish et al., "Molecular Cell Biology," Scientific American Books, pp. 280-281, 1986.

Mainous et al., "Nasal Carriage of *Staphylococcus aureus* and Methicillin-Restraint *S aureus* in the United States, 2001-2002," Ann Fam Med Mar. 1, 2006 vol. 4 No. 2 132-137.

Nicholson et al., "Binding of DNA in vitro by a small, acid-soluble spore protein from Bacillus subtilis and the effect of this binding on DNA topology," J. Bacteriol. Dec. 1990 vol. 172 No. 12 6900-6906.

Noskin et al., "The Burden of *Staphylococcus aureus* Infections on Hospitals in the United States," Arch Intern Med. 2005; 165(15):1756-1761.

Resch et al., "Comparatie Proteome Analysis of *Staphylococcus aureus* Biofilm and Planktonic Cells and Correlation with Transcriptome Profiling," Proteomics 2006, 6 1867-1877.

Robinson et al., "Re-emergence of early pandemic *Staphylococcus aureus* as a community-acquired meticillinresistant clone," The Lancet, vol. 365, Issue 9466, Apr. 2-8, 2005, pp. 1256-1258.

Schenk et al. "Improved method for electroporation of *Staphylococcus aureus*," FEMS Microbiology Letters vol. 94, Issues 1-2, Jul. 1, 1992, pp. 133-138.

Setlow et al., "Mutation and killing of *Escherichia coli* expressing a cloned *Bacillus subtilis* gene whose product alters DNA conformation," J. Bacteriol. May 1992;174(9):2943-50.

Setlow, "Spores of Bacillus subtilis: their resistance to and killing by radiation, heat and chemicals," Journal of Applied Microbiology vol. 101, Issue 3, pp. 514-525, Sep. 2006.

Singleton et al. "Dictionary of Microbiology and Molecular Biology Second Edition," excerpt defining "constitutive." 1987.

Yoichi et al., "Alteration of tail fiber protein gp38 enables T2 phage to infect *Escherichia coli* O157:H7" Journal of Biotechnology vol. 115, Issue 1, Jan. 12, 2005, pp. 101-107.

* cited by examiner

B1003 (SEQ ID NO. 3)
5′ - CGGGATCCGACTAAAAATTAGTCG - 3′

B1004 (SEQ ID NO. 4)
5′ - GGACTAGTGAATGAGTATCATCATGGAGG - 3′

B1005 (SEQ ID NO. 5)
5′ - CGATGGATCCTCTCATTTATAAGGTTAAATAATTC - 3′

B1006 (SEQ ID NO. 6)
5′ - GCAGACCGCGGCTATTTATCCTTCACTCTCATC - 3′

B1007 (SEQ ID NO. 7)
5′ - CTACGGATCCTTTATCCTCCAATCTACTTATAAA - 3′

B1008 (SEQ ID NO. 8)
5′ - CATGCCATGGAAGTTCCTCCTTGAGTGCT - 3′

B1009 (SEQ ID NO. 9)
5′ - CGATCCATGGCAAATTATCAAAACGC - 3′

B1010 (SEQ ID NO. 10)
5′ - AGTGAGATCTGAATTCGCTGATTAAAAGAAAC - 3′

ϕ11 Lysogen / ϕ11 orf 51
holin
amidase

PTL1003 / PTSA1.2/A

**Reduction in viability of *S. aureus* cells infected with SASPject PTSA1.2/A**

A strain of *S. aureus* was grown to a density of $5 \times 10^7$ cells/ml. The culture was then split and product PTSA1.2/A ($1 \times 10^{10}$ particles) was added to one aliquot and incubation continued. Samples were taken at 30 min and hourly post infection to enumerate the number of viable bacteria remaining.

Figure 6

**Comparison of *S. aureus* cells infected with SASPject PTSA1.2/A ($\phi$11:holin$^-$::SASP-C$^+$) vs SA0/A ($\phi$11:holin$^-$::SASP-C$^-$)**

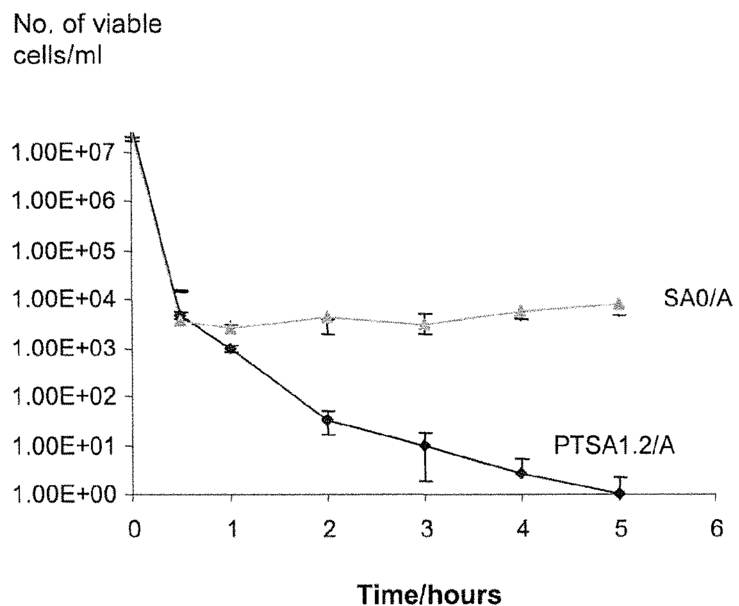

A strain of *S. aureus* was grown to a density of 5 x$10^7$ cells/ml. The culture was then split - product PTSA1.2/A (1 x $10^{10}$ particles) was added to one aliquot and phage SA0/A (1 x $10^{10}$ particles) was added to one aliquot and incubation continued. Samples were taken at 30 min and hourly post infection to enumerate the number of viable bacteria remaining.

Figure 7

**Graph showing effect of SASPject PTSA1.2/A upon a PTSA1.2/A monolysogen of *S. aureus*.**

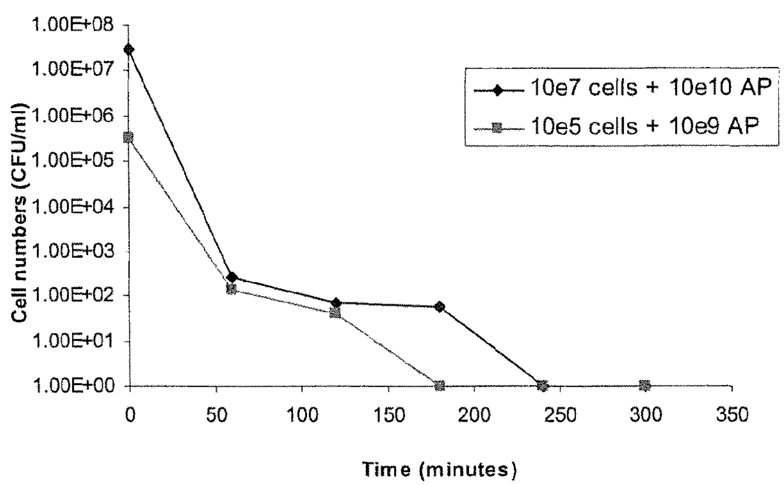

A strain of *S. aureus* lysogenised with PTSA1.2/A was grown to a density of either $5 \times 10^7$ cells/ml or $5 \times 10^5$ cells/ml. To cells at a density of $5 \times 10^7$ cells/ml, $1 \times 10^{10}$ PTSA1.2/A particles were added and to cells at a density of $5 \times 10^5$ cells/ml, $1 \times 10^9$ PTSA1.2/A particles were added. Samples were taken at 30 min and hourly post infection to enumerate the number of viable bacteria remaining.

MODIFIED BACTERIOPHAGE

CROSS REFERENCE TO RELATED APPLICATIONS

This application is a divisional of U.S. application Ser. No. 15/147,483, filed May 5, 2016, now U.S. Pat. No. 10,106,784, which is a divisional of U.S. application Ser. No. 14/190,727, filed Feb. 26, 2014, now U.S. Pat. No. 9,359,596, which is a divisional of U.S. application Ser. No. 12/672,311, filed Jun. 3, 2010, now U.S. Pat. No. 8,697,049, which is a 371 National Stage of International Application No. PCT/EP08/60360 filed Aug. 6, 2008, which claims priority to International GB Appl. No. 0715416.4, filed Aug. 7, 2007, the contents of all of which are incorporated by reference herein in their entireties.

SEQUENCE LISTING

This application includes a sequence listing which has been submitted via EFS-Web in a file named "43297o2004txt" created Sep. 11, 2018 and having a size of 2,240 bytes, which is hereby incorporated by reference in its entirety.

The present invention relates to modified bacteriophage and a process for the production of modified bacteriophage.

BACKGROUND TO THE INVENTION

*Staphylococcus aureus* is the most common cause of infections contracted whilst in hospital (nosocomial infections) (Noskin et al., 2005). It frequently causes infections in the lungs, wounds, skin and the blood and, because of the number of toxins the bacterium can produce, these infections may be life threatening.

Almost all strains of *S. aureus* are now resistant to penicillin owing to their ability to produce an enzyme (penicillinase) which breaks down the drug; and 45 years after the introduction of methicillin in 1959, a penicillinase-resistant penicillin, methicillin resistant *S. aureus* (MRSA) strains are endemic in many hospitals. More recently MRSA strains have also become a problem in the community. Many MRSA strains are now resistant to multiple antibiotics.

MRSA levels have risen dramatically in hospitals in both the US and the UK and, in addition, new Community Acquired MRSA (CA-MRSA) strains have spread rapidly across the globe since they were first reported in the late 1990's. These CA-MRSA strains have proven to be highly transmissible and often carry a set of genes encoding Panton Valentine Leukocidin which is a toxin that can make these strains highly virulent. There are concerns that these CA-MRSA strains may further add to the difficulties of controlling MRSA infections in hospitals (Donegan, 2006).

In fact, MRSA is now such a serious (and lethal) problem in hospitals that significant effort is being put into implementing infection control measures as a way of minimising the spread of MRSA in hospitals and thus reducing the number of infections. In relation to MRSA in particular, infection control measures include, variously, the use of hand sanitisers by healthcare workers; screening, isolation and barrier nursing of infected and carrier patients; and decontamination of patients and healthcare workers who carry MRSA. The carriage of bacteria is defined as the presence of bacteria, usually at a low level, without any associated pathology such as inflammation. However, MRSA carriers do constitute a significant risk for the spread of MRSA to the wider hospital community, and the elimination of MRSA from carriers, particularly on or prior to admission, is a very important part of the infection control process.

Carriage of *S. aureus* (and therefore MRSA) occurs in and around the nose, armpits, groin, and perineum as well as in superficial skin lesions. A number of studies report that *S. aureus* is carried in the nose by 25 to 30% of the general population with MRSA being carried by around 1%. Amongst hospital patients the carriage rate is significantly higher. In the US it has been estimated that 89 million people carry *S. aureus* in their nose, and 2.3 million of those carry MRSA (Mainous et al., 2006). The intra-nasal elimination of MRSA is therefore fundamental to controlling the spread of this potentially lethal organism in hospitals.

As an alternative to conventional antibiotics, one family of proteins which demonstrate broad spectrum antibacterial activity inside bacteria comprises the $\alpha/\beta$-type small acid-soluble spore proteins (known henceforth as SASP). Inside bacteria, SASP bind to the bacterial DNA: visualisation of this process, using cryoelectron microscopy, has shown that SspC, the most studied SASP, coats the DNA and forms protruding domains and modifies the DNA structure (Francesconi et al., 1988; Frenkiel-Krispin et al., 2004) from B-like (pitch 3.4 nm) towards A-like (3.18 nm; A-like DNA has a pitch of 2.8 nm). The protruding SspC motifs interact with adjacent DNA-SspC filaments packing the filaments into a tight assembly of nucleo-protein helices. In this way DNA replication is halted and, where bound, SASP prevent DNA transcription. SASP bind to DNA in a non-sequence specific manner (Nicholson et al, 1990) so that mutations in the bacterial DNA do not affect the binding of SASP.

WO02/40678 describes the use as an antimicrobial agent of bacteriophage modified to incorporate a SASP gene. In order to provide effective production of the modified bacteriophage in a bacterial host, WO02/40678 aims to avoid expression of the SASP gene during proliferation of the production host. To this end, the SASP gene was preferably inserted into the lysis genes of the bacteriophage so as to put the SASP gene under the control of a lysis gene promoter which is active only at the end of the bacteriophage life cycle. It was thought that proliferation of the bacterial production host would otherwise be prevented owing to the presence of the SASP gene product, particularly if the SASP gene was under the control of a constitutive promoter. In a less preferred arrangement, the SASP gene could be located elsewhere on the bacteriophage chromosome and placed under the control of a bacteriophage or bacterial promoter whereby the lytic cycle could be left to run its course. In this arrangement, the bacterial promoter would be non-constitutive and could be up-regulated by environmental cues.

SUMMARY OF THE INVENTION

It has now surprisingly been found that effective production of bacteriophage may be achieved where the bacteriophage has been modified to carry a gene encoding a SASP under the control of a promoter which is controlled independently of the bacteriophage, and which is constitutive with no exogenous or in trans regulation necessary or provided, When present in multiple copies, for example following infection of target cells, the promoter. drives toxic levels of SASP expression.

Accordingly, in a first aspect, the present invention provides a modified bacteriophage capable of infecting a target bacterium, which bacteriophage includes an $\alpha/\beta$ small acid-soluble spore protein (SASP) gene encoding a SASP which is toxic to the target bacterium, wherein the SASP gene is under the control of a constitutive promoter which is foreign to the bacteriophage and the SASP gene.

In a second aspect, there is provided a process for the production of a modified bacteriophage capable of infecting a target bacterium, which process comprises growing a bacterial host comprising genetic material encoding the bacteriophage in a growth medium; causing the bacteriophage to replicate in the bacterial host; and harvesting the bacteriophage.

Use of a modified bacteriophage in which the SASP gene is under the control of a constitutive promoter has a number of advantages. Control of expression of the SASP gene is removed from the bacteriophage whereby production of SASP becomes independent of phage gene expression. This enables the SASP to be produced even when the bacteriophage cannot carry out its full life cycle; which may happen in the case of super-infection (where the bacteriophage infects a bacterial host already carrying a prophage) and host restriction of the bacteriophage DNA. As described below this strategy thus allows one phage type to inhibit many different strains of one bacterial species.

Whilst bacteriophage generally tend to have narrow host ranges, putting a SASP gene under the control of a constitutive promoter can broaden the host range of the modified bacteriophage. This is because one of the key ways in which bacteria limit their host range is by degrading bacteriophage DNA on entry into a bacterial cell. Use of bacteriophage to deliver aSASP gene, whose production is independent of the bacteriophage, means that the fate of the bacteriophage DNA may not impact on the efficacy of the SASP. In this way, the bacteriophage acts as a delivery vector by delivering the gene encoding the SASP to a target bacterial cell.

Production of a modified bacteriophage according to the invention requires a bacterial host which can be lysogenised by the bacteriophage. This lysogen should allow proliferation of the bacteriophage upon induction, so that an adequate bacteriophage titre may be obtained for harvesting. According to the invention, the SASP do not prevent the production of adequate phage titres within the timescale required by a manufacturing process, i.e. prior to host cell death.

A preferred approach according to the present invention is to use a constitutive promoter to control the SASP gene, such that the promoter does not promote the expression of sufficient SASP to kill the host production strain from which the modified bacteriophage is to be harvested. The promoter may be a bacterial promoter, such as from *S. aureus*. Preferred promoters include the *S. aureus* promoters pdhA for pyruvate dehydrogenase E1 component alpha subunit, rpsB for the 30S ribosomal protein S2, pgi for glucose-6-phosphate isomerase. Sequences having >90% identity to these sequences may also be used on promoters according to the invention. A particularly preferred promoter is the promoter for the fructose bisphosphate aldolase gene, fbaA, from *S. aureus* N315 (accession no. BAB43211), or a sequence showing >90% homology to this sequence. An advantage of using the fbaA promoter to express the SASP gene is that this promoter expresses constitutively in bacterial cells and does not appear to be regulated by any mechanism within *S. aureus* cells. In addition, a single copy of the fbaA::SASP-C element does not produce enough SASP-C to be lethal to a host cell, enabling maintenance and production of the PTSA 1.2/A bacteriophage, as described in further detail below. Upon infection of target bacteria, however, multiple copies of the fbaA promoter (from multiple infection events or phage replication within the target cell) drives sufficient expression of SASP-C so as to cause loss of viability of the target.

Thus promoters which are suitable to be used upstream of SASP in bacteriophage constructs, such as the fbaA promoter, have two defining properties; they are not strong enough to kill the bacteriophage's host during growth of the host bacterium; they do not prevent the production of adequate phage titres within the timescale required by a manufacturing process, i.e. prior to host cell death. However, they are sufficiently strong so as to drive the production of toxic levels of SASP when present in multiple copies, i.e. following delivery of multiple copies of the SASP gene to a targeted cell or due to phage replication in a targeted cell. Selection of promoters with such activities may be made by analysing bacteriophage constructs for these characteristics.

The promoter controlling transcription and therefore expression of the SASP gene is foreign to both the bacteriophage and the SASP gene in the sense that it does not originate from the bacteriophage and is not the native promoter of the SASP gene. In this way, control of expression of the SASP gene is divested from the phage.

The bacterial host can be any host suitable for a given bacteriophage. The host must support the bacteriophage through the proliferation of mature bacteriophage particles within the host, when induced to do so. WO02/40678 sets out in appendix 4 a list of common pathogens and some of their phages. This appendix is reproduced in the present application as appendix 1. *Staphylococcus* and *Clostridium* hosts, preferably *Staphylococcus aureus* and *Clostridium difficile*, are particularly useful hosts. Bacteriophage ø11 is capable of infecting *Staphylococcus aureus* and is described in further detail below. This bacteriophage may be modified in accordance with the present invention.

Sequences of α/ß-type SASP may be found in appendix 1 of WO02/40678, including SASP-C from *Bacillus megaterium* which is the preferred α/ß-type SASP.

Bacteriophage vectors modified to contain a SASP gene have generally been named SASPject vectors. SASPject vector PTSA1.2/A is described in further detail below for delivery of the SASP gene to *S. aureus*, including MRSA. Once the SASP gene has been delivered to a target bacterium, SASP is produced inside those bacteria where it binds to bacterial DNA and changes the conformation of the DNA from B-like towards A-like. Production of sufficient SASP inside target bacterial cells causes a drop in viability of affected cells; thus toxicity caused by SASP is dose dependent, which in turn is dependent upon promoter activity and number of promoter::SASP copies present.

In general, the SASP gene and its promoter may be placed anywhere within the bacteriophage genome. However, it is preferred for targeting pathogenic bacteria that the modified bacteriophage is non-lytic and this may be achieved by the removal or inactivation of one or more genes required by the phage for lysing infected bacteria, most preferably by inactivating at least one of the lysis genes. In a preferred embodiment, the SASP gene is inserted into one of the lysis genes or the lysis gene is replaced with the toxin gene. The genes for lysing infected bacteria include the bacteriophage holin gene and/or an amidase gene. One or more of these genes may be interrupted or replaced by the SASP gene. Preventing the modified bacteriophage from lysing its target bacterial host allows continued expression and accumulation of the SASP, possibly beyond the time at which the bacteriophage would normally cause the bacterial host to lyse.

In a further aspect, the present invention provides a composition for inhibiting or preventing bacterial cell growth, which comprises a modified bacteriophage as defined herein and a carrier therefor. Such a composition may have a wide range of uses and is therefore to be formulated according to the intended use. The composition may be formulated as a medicament, especially for human treatment and may treat various conditions, including bacterial infections. Among those infections treatable according to the present invention are topical infections, dental carries, respiratory infections, eye infections and localised tissue and organ infections. The carrier may be a pharmaceutically-acceptable recipient or diluent. The exact nature and quantities of the components of such compositions may be determined empirically and will depend in part upon the routes of administration of the composition.

Routes of administration to recipients include oral, buccal, sublingual, intranasal, by inhalation, topical (including ophthalmic), intravenous, intra-arterial, intra-muscular, subcutaneous and intra-articular. For convenience of use, dosages according to the invention will depend on the site and type of infection to be treated or prevented. Respiratory infections may be treated by inhalation administration and eye infections may be treated using eye drops. Oral hygiene products containing the modified bacteriophage are also provided; a mouthwash or toothpaste may be used which contains modified bacteriophage according to the invention formulated to eliminate bacteria associated with dental plaque formation.

A modified bacteriophage according to the invention may be used as a bacterial decontaminant, for example in the treatment of surface bacterial contamination as well as land remediation or water treatment. The bacteriophage may be used in the treatment of medical personnel and/or patients as a decontaminating agent, for example in a handwash. Treatment of work surfaces and equipment is also provided, especially that used in hospital procedures or in food preparation. One particular embodiment comprises a composition formulated for topical use for preventing, eliminating or reducing carriage of bacteria and contamination from one individual to another. This is important to limit the transmission of microbial infections, particularly in a hospital environment where bacteria resistant to conventional antibiotics are prevalent. For such a use the modified bacteriophage may be contained in Tris buffered saline containing $CaCl_2$ (10 mM) and $MgCl_2$ (1 mM) or may be formulated within a gel or cream. For multiple use a preservative may be added. Alternatively the product may be lyophilised and excipients, for example a sugar such as sucrose may be added.

DETAILED DESCRIPTION OF THE INVENTION

The present invention will now be described in further detail, by way of example only, with reference to the accompanying drawings and the following example.

BRIEF DESCRIPTION OF THE DRAWINGS

FIG. 6. A kill curve comparing the killing ability of PTSA1.2/A with the same phage minus the SASP gene.

FIG. 7. A kill curve of PTSA1.2/A infecting an *S. aureus* strain.

SUMMARY OF CONSTRUCTION OF A GENETICALLY ALTERED BACTERIOPHAGE CARRYING SASP-C UNDER CONTROL OF A FRUCTOSE BISPHOSPHATE ALDOLASE HOMOLOGUE (FBAA) PROMOTER

Genes can be removed and added to the phage genome using homologous recombination. There are several ways in which phages carrying foreign genes and promoters can be constructed and the following is an example of such methods.

For the construction of a ϕ11 derivative it is shown how, using an *E. coli/S. aureus* shuttle vector, as an example only, the phage holin gene has been replaced with the gene for SASP-C, under the control of a *S. aureus* fructose bisphosphate promoter homologue (fbaA is used from this point on to denote the fructose bisphosphate aldolase promoter). Genes for resistance to the heavy metal Cadmium (referred to henceforth as $Cd^R$) are used as a non-antibiotic resistance marker.

The fbaA-SASP-C and $Cd^R$ regions were cloned between two regions of ϕ11 DNA which flank the ϕ11 holin gene. Subsequently, this plasmid was introduced into cells and double recombinants were selected for, where the holin was replaced with the fbaA-SASP-C and $Cd^R$ region.

EXPERIMENTAL PROCEDURES

All PCR reactions were performed using Expand High Fidelity PCR system and stringent conditions, depending upon the melting temperatures ($T_m$) of the primers, according to the manufacturers instructions. Unless otherwise stated, general molecular biology techniques, such as restriction enzyme digestion, agarose gel electrophoresis, T4 DNA ligase-dependent ligations, competent cell preparation and transformation were based upon methods described in Sambrook et al. (1989). DNA was purified from enzyme reactions and prepared from cells using Qiagen DNA purification kits. *S. aureus* cells were transformed with plasmid DNA by electroporation, using methods such as those described by Schenck and Ladagga (1992).

Primers were obtained from Sigma Genosys. Where primers include recognition sequences for restriction enzymes, an extra 2-6 nucleotides was added at the 5' end to ensure digestion of amplified PCR DNA.

All clonings, unless otherwise stated, are achieved by ligating DNAs overnight with T4 DNA ligase and then transforming them into *E. coli* cloning strains, such as DH5α or XL1-Blue, with isolation on selective medium, as described elsewhere (Sambrook et al., 1989)

An *E. coli/S. aureus* shuttle vector, designated pSM198 was used to transfer to genes between *E. coli* and *S. aureus*. Plasmid pSM198 was previously produced by combining *E. coli* cloning vector pUC18 and the tetracycline resistance and replication regions of *S. aureus* plasmid pT181. The plasmid carries resistance markers that can be selected for in *E. coli* and *S. aureus*. This plasmid retains the pUC18 multiple cloning site (MCS), although not all the sites remain as unique sites. The remaining unique sites in the MCS of pSM198 are: PstI, SalI, BamHI, SacI and EcoRI.

Figure 1:
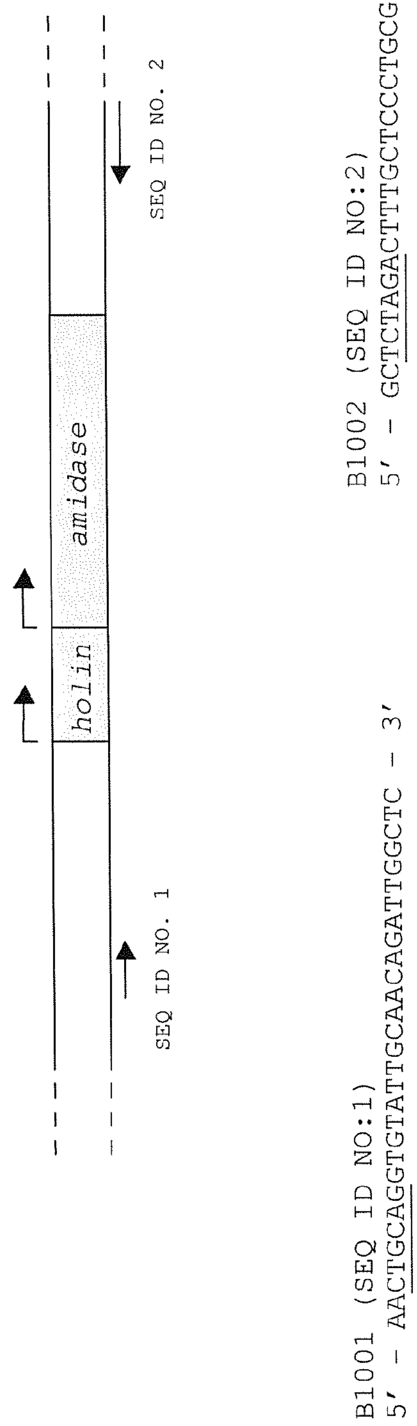
FIG. 1. Region of *S. aureus* phage ϕ11, showing the holin and amidase genes, and the priming sites for amplification of the genes and flanking DNA FIG. 2. Diagram of pSA1, showing the cloned region and the location of the priming sites for inverse PCR of pSA1.

Construction of a Plasmid for Targeted Replacement of the ϕ11 Holin Gene with fbaA-SASP-C/Cd$^R$ 1. Plasmid pSA1, comprising pBluescript SK+ containing a 1.8 kb fragment of ϕ11 spanning the lytic genes, was constructed as follows. FIG. 1 shows the priming sites for the oligonucleotides described below for amplification of regions from the ϕ11 genome.

PCR amplification of ϕ11 DNA using primers B1001 and B1002, was carried out and yielded a 1.8 kb fragment which was cleaned and digested with XbaI and PstI. After digestion, the DNA was cleaned and cloned into XbaI and PstI digested pBluescript SK+, yielding pSA1.

Primer B1001 (SEQ ID NO: 1) comprises a 5' PstI site (underlined) followed by sequence of ϕ11 (Genbank: AF424781) from base 39779 to base 39798, (see FIG. 1). Primer B1002 (SEQ ID NO: 2) comprises an XbaI site (underlined) followed by the reverse and complement of sequence of ϕ11 from base 41537 to base 41556 (see FIG. 1).

```
B1001
                                    (SEQ ID NO: 1)
5'-AACTGCAGGTGTATTGCAACAGATTGGCTC-3'

B1002
                                    (SEQ ID NO: 2)
5'-GCTCTAGACTTTGCTCCCTGCGTCGTTG-3'
```

Figure 2:
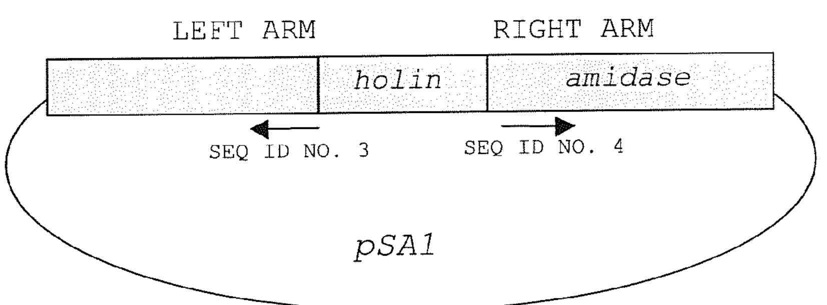

2. Inverse PCR was carried out on pSA1 as the template, using primers B1003 (SEQ ID NO: 3) and B1004 (SEQ ID NO: 4) (see FIG. 2).

Primer B1003 comprises a 5' BamHI site (underlined) followed by the reverse and complement sequence of ϕ11 from base 40454 to base 40469 (see FIG. 1). Primer B1004 comprises a 5' SpeI site (underlined), followed by sequence of ϕ11 from base 40891 to base 40911 (see FIG. 2).

```
B1003
                                    (SEQ ID NO. 3)
5'-CGGGATCCGACTAAAAATTAGTCG-3'

B1004
                                    (SEQ ID NO. 4)
5'-GGACTAGTGAATGAGTATCATCATGGAGG-3'
```

This PCR reaction yielded an ~4.2 kb fragment which constituted: ϕ11 left arm, the entire pBluescript SK+ plasmid, and the ϕ11 right arm. This fragment was digested with BamHI and SpeI, cleaned, and subsequently used as a vector to clone in the following fragment.

3. The cadmium resistance region from pI258 was amplified by PCR using primers B1005 and B1006, yielding an ~2.8 kb fragment. The PCR product was cleaned and digested with BamHI and XbaI. The digested PCR product was cleaned and cloned into pSA1 (PCR amplified and digested, above), making pSA2.

Primer B1005 (SEQ ID NO: 5) is complementary to DNA 308 bp upstream from the ATG for the putative cadmium-responsive regulatory protein gene cadC from pI258 (Genbank: J04551), the 3' end being nearest the ATG (see FIG. 3). The 5' end of the primer carries a non-complementary tail with a BamHI site (underlined) to aid cloning.

Figure 3:
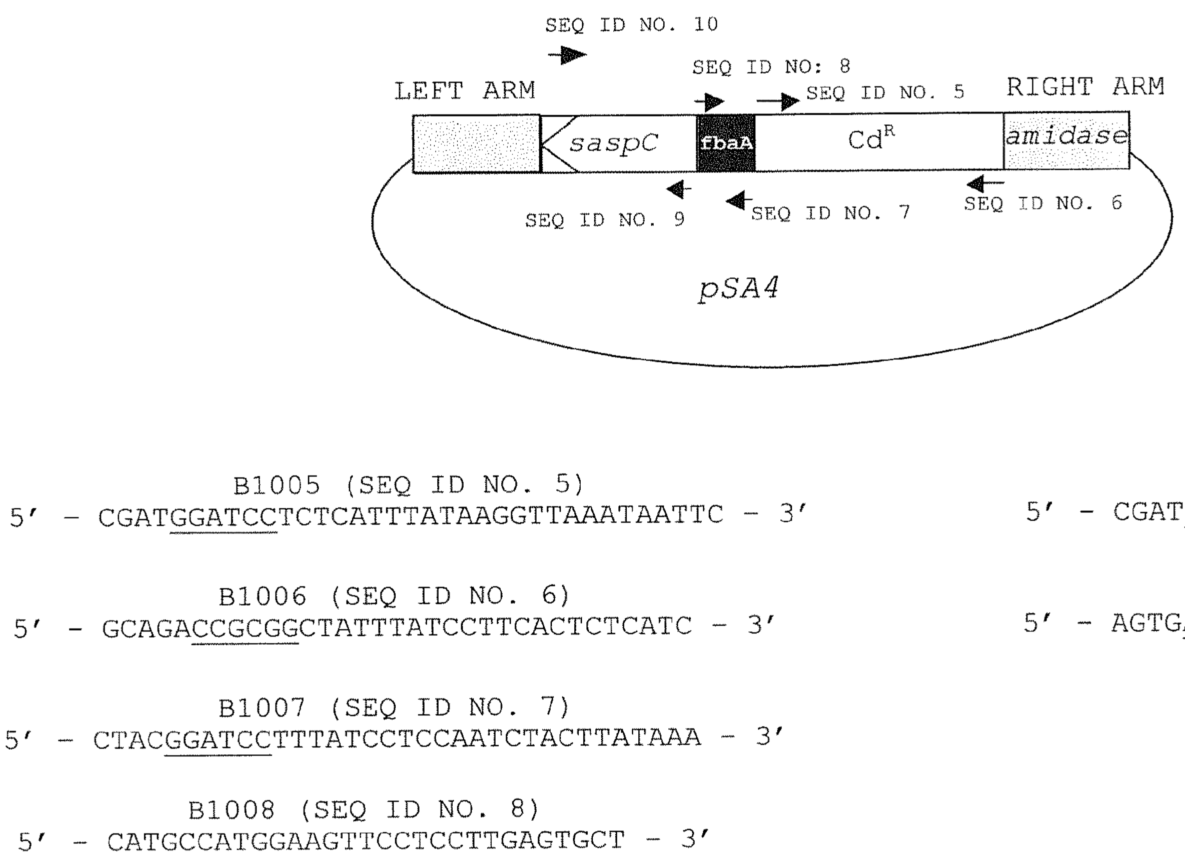
FIG. 3. Diagram of pSA4, showing the cloned promoter-saspC region with the cadmium resistance ($Cd^R$) gene and the flanking ϕ11 DNA, together with the location of relevant priming sites.

Primer B1006 (SEQ ID NO: 6) is complementary to DNA at the 3' end of the cadA gene for the cadmium resistance protein from plasmid pI258, such that the last 3 complementary nucleotides are complementary to the stop codon TAG of the cadA gene (see FIG. 3). The 5' end carries a non-complementary XbaI site (underlined) to aid cloning.

```
B1005
                                    (SEQ ID NO: 5)
5'-CGATGGATCCTCTCATTTATAAGGTTAAATAATTC-3'

B1006
                                    (SEQ ID NO: 6)
5'-GCAGACCGCGGCTATTTATCCTTCACTCTCATC-3'
```

4. The DNA containing the ϕ11 left and right arms and Cd$^R$ were cut out of pSA2 using PstI and SacI, and gel purified away from the vector. This fragment was cloned into shuttle vector pSM198 which was also cut PstI and SacI. Clones were screened for the restriction fragment and candidates were sent for sequencing. A correct plasmid construct was identified and named pSA3. This plasmid was used to clone in the following fragments.

5. PCR amplification of the fbaA promoter using B1007 and B1008 yielded an approximately 300 bp fragment which was cleaned and subsequently digested with NcoI, then re-cleaned.

The fbaA PCR fragment was ligated to the SASP-C coding sequence from *B. megaterium*. The amplification and preparation of the SASP-C gene is described below.

Primer B1007 (SEQ ID NO: 7) comprises a 5' sequence tail which includes a BamHI site, followed by the reverse complement of bases 2189404 to 2189427 from the *S. aureus* NCTC 8325 genome (Genbank: CP000253) (see FIG. 3).

Oligonucleotide B1008 (SEQ ID NO: 8) comprises a sequence tail which includes an NcoI site, then the sequence of bases 2189214 to 2189232 from the *S. aureus* NCTC 8325 genome (see FIG. 3). When a PCR product is made using this primer, the NcoI site incorporated into the primer at the ATG of the gene results in the change of the base 2 nucleotides upstream of the ATG from T>C.

```
B1007
                                    (SEQ ID NO: 7)
5'-CTACGGATCCTTTATCCTCCAATCTACTTATAAA-3'

B1008
                                    (SEQ ID NO: 8)
5'-CATGCCATGGAAGTTCCTCCTTGAGTGCT-3'
```

6. The SASP-C gene from *B. megaterium* strain KM (ATCC 13632) was amplified by PCR with primers B1009 and B1010 and yielded an ~300 bp fragment. The PCR product was cleaned and digested with NcoI. The digested PCR product was cleaned and used in a ligation with the fbaA PCR fragment, as described below.

Oligonucleotide B1009 (SEQ ID NO: 9) comprises a 5' tail containing an NcoI site and is complementary to the first 20 nucleotides of SASP-C (accession no. K01833), starting at the ATG, from *B. megaterium* strain KM (see FIG. 3). The NcoI site at the beginning of the oligonucleotide incorporates the ATG of the SASP-C gene.

```
B1009
                                    (SEQ ID NO: 9)
5'-CGATCCATGGCAAATTATCAAAACGC-3'
```

Oligonucleotide B1010 (SEQ ID NO: 10) comprises a BglII site (underlined), and an EcoRI site (double underlined), followed by the reverse complement of DNA starting 59 bases downstream of the stop codon to 74 bases downstream of the stop codon of the SASP-C gene (see FIG. 3).

```
B1010
                                        (SEQ ID NO: 10)
5'-AGTGAGATCTGAATTCGCTGATTAAAAGAAAC-3'
```

7. The fbaA and the SASP-C PCR fragments (both cut NcoI) were ligated together using T4 DNA ligase. The ligated DNAs were used as a template for PCR, to amplify the joined fbaA and SASP-C DNAs. PCR was performed using primers B1007 and B1010. The main PCR product of ~500 bp was gel purified. The PCR product was digested with BamHI and BglII and cleaned. This fragment was cloned into pSA3 which was prepared as follows. The plasmid was cut with BamHI, and the ends were dephosphorylated using calf intestinal alkaline phosphatase (CIAP). The DNA was cleaned again.

Plasmids were screened so that the end of the SASP-C gene was adjacent to the "left arm" region of ϕ11, and so the start of the fbaA promoter was adjacent to the cadmium chloride resistance region. The resulting plasmid, carrying fbaA-SASP-C, was named pSA4.

Replacement of the Holin Gene from *S. aureus* Phage ϕ11 with fbaA-SASP-C and the $Cd^R$ Marker 1. pSA4 was transformed into *S. aureus* strain PTL47. PTL47 is a monolysogen of ϕ11 in RN4220.

2. Cells which had undergone a double crossover, where the DNA contained between the ϕ11 left and right arms of pSA4 have replaced the DNA between the ϕ11 left and right arms in the phage genome (ie the holin gene) gave rise to colonies with the following phenotype: $CdCl_2$ (0.1 mM) resistant, tetracycline (5 μg/ml) sensitive. Tetracycline resistance is carried by the shuttle vector pSM198. Loss of tetracycline resistance is indicative of loss of pSM198. Colonies which had the phentoype: $CdCl_2^R$, $tetracycline^S$ were screened further by colony PCR.

3. PCR reactions were performed to check that the holin gene was no longer present, and that the fbaA-SASP-C and the $CdCl_2^R$ gene were present and correctly placed in the ϕ11 prophage genome. PCR fragments were sequenced to ensure that the isolate carried the expected sequence, especially in regions: fbaA and SASP-C.

Verified prophage constructs were thus identified and a representative was picked and named PTL1001.

4. Phage was induced from a culture of strain PTL1001 by heat shock, and the cells were lysed with lysostaphin (0.25 μg/ml), and then filtered through a 0.2 μm filter, yielding a crude cell-free phage lysate.

5. This lysate was used to infect *S. aureus* strain 8325-4. The infection mixture was plated onto ϕVPB (vegetable peptone brothcontaining 10 g/l sodium chloride)+$CdCl_2$ (0.1 mM) agar plates to select for lysogens after overnight growth at 37° C.

6. Lysogens were checked by colony PCR as described above. A verified lysogen was identified and named PTL1002.

7. PTL1002 was passaged 5 times on ϕVPB agar, picking a single colony and re-streaking to single colonies at each passage.

Figure 4:
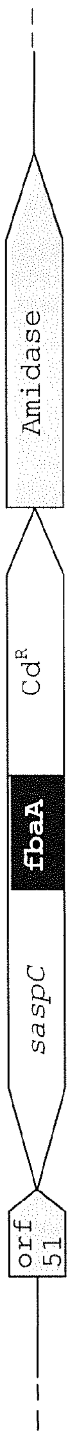
FIG. 4. Arrangement of DNA within the genome of PTL1003, showing the replacement of the holin gene with foreign genes. The arrangement of genes in the wild-type ϕ11 genome is shown for comparison.

8. A single colony was picked and analysed again by PCR and sequencing. The verified isolate was named PTL1003. The phage carried by this lysogen strain is called PTSA1.2/A (see FIG. 4).

Figure 5:
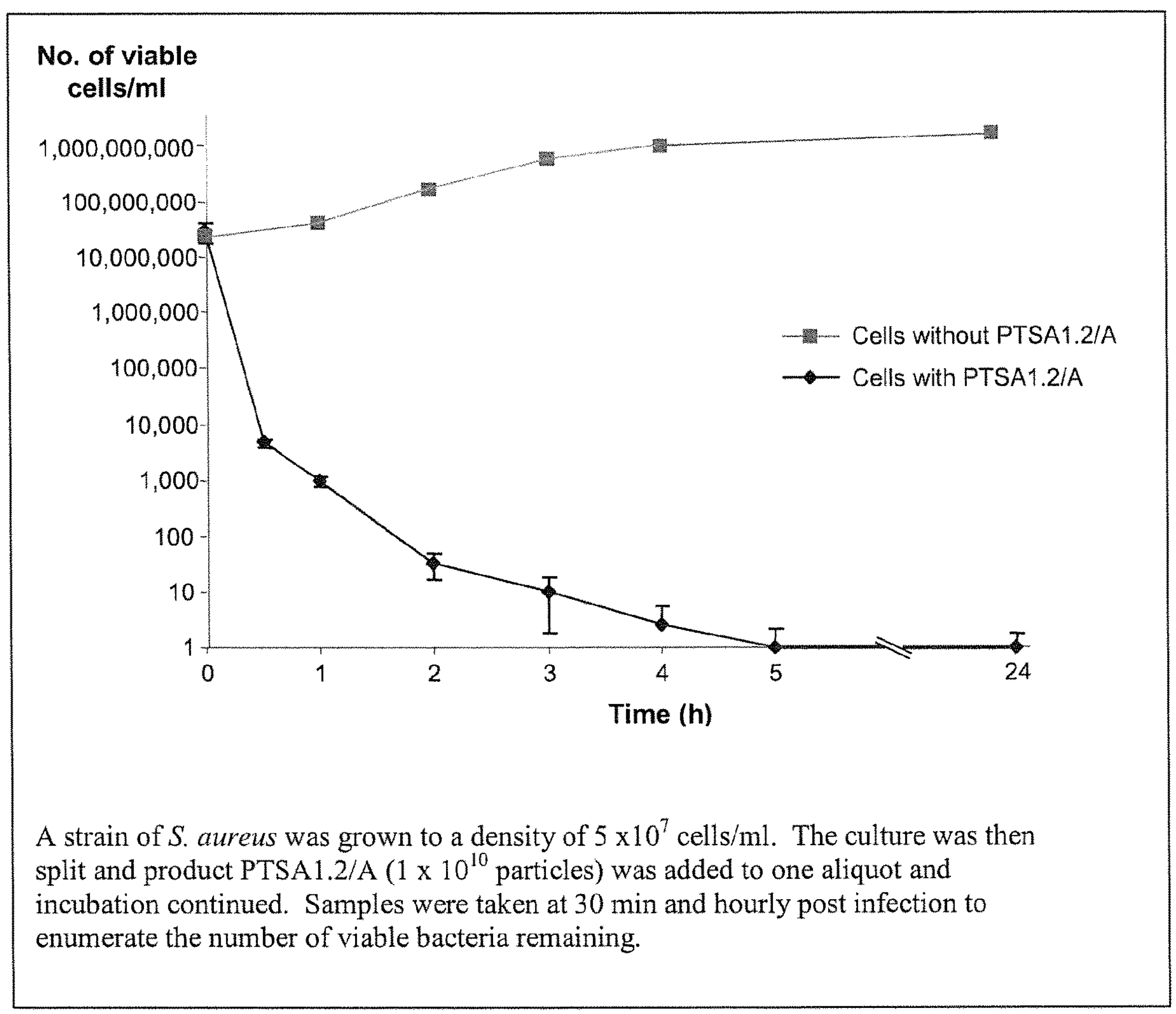
FIG. 5. An example of a kill curve showing efficacy of PTSA1.2/A against an *S. aureus* strain.

SASPject vector PTSA1.2/A has been tested against a panel of *S. aureus* strains and clinical isolates, including methicillin sensitive *S. aureus* (MSSA) and MRSA strains belonging to each of the 5 recognised scc-mec types. An example of a kill curve showing efficacy of PTSA1.2/A against an *S. aureus* strain is given in FIG. 5.

A kill curve comparing the killing ability of PTSA1.2/A versus the same phage minus the SASP gene (phage SA0/A) is given in FIG. 6, and confirms that the kill rate is due to presence of the SASP.

A kill curve of PTSA1.2/A infecting an *S. aureus* strain which is a monolysogen of PTSA1.2/A is given in FIG. 7, and shows that superinfection immunity to the phage does not prevent SASP from inhibiting infected cells.

REFERENCES

Donegan, N. 2006. Annual Meeting of the Soc. for Healthcare Epidemiology of America.

Francesconi, S. C., MacAlister, T. J., Setlow, B., and Setlow, P. 1988. Immunoelectron microscopic localization of small, acid-soluble spore proteins in sporulating cells of *Bacillus subtilis*. J. Bacteriol. 170: 5963-5967.

Frenkiel-Krispin, D., Sack R., Englander, J., E. Shimoni, Eisenstein, M., Bullitt, Horowitz-Scherer, E. R., Hayes, C. S., Setlow, P., Minsky, A., and Wolf, S. G. 2004. Structure of the DNA-SspC Complex: Implications for DNA Packaging, Protection, and Repair in Bacterial Spores. J. Bacteriol. 186: 3525-3530.

Mainous, A. G. III, Hueston, W. J., Everett, C. J., and Diaz V. A. 2006. Nasal Carriage of *Staphylococcus aureus* and Methicillin Resistant *S. aureus* in the US 2001-2002. *Annals of Family Medicine* 4:132-137.

Nicholson, W. L., Setlow, B., and Setlow, P. 1990. Binding of DNA in vitro by a small, acid-soluble spore protein from *Bacillus subtilis* and the effect of this binding on DNA topology. J. Bacteriol. 172: 6900-6906.

Noskin, G. A., Rubin, R. J., Schentag, J. J., Kluytmans, J., Hedblom, E. C., Smulders, M., Lapetina, E., and Gemmen, E. 2005. The Burden of *Staphylococcus aureus* Infections on Hospitals in the United States: An Analysis of the 2000 and 2001 Nationwide Inpatient Sample Database. *Arch Intern Med* 165: 1756-1761

Sambrook, J., Fritsch, E. F. and Maniatis, T. in *Molecular Cloning, A Laboratory Manual* 2nd edn (Cold Spring Harbor Press, New York, 1989).

Schenk, S., and R. A. Laddaga. 1992. Improved method for electroporation of *Staphylococcus aureus*. FEMS Microbiol. Lett. 73:133-138.

APPENDIX 1

A list of common pathogens and some of their phages. (This list is representative but not exhaustive).

Coliphages:

| | |
|---|---|
| Bacteriophage | lambda |
| Bacteriophage | 933W (*Escherichia coli* O157:H7) |
| Bacteriophage | VT2-Sa (*E. coli* O157:H7) |
| Coliphage | 186 |
| Coliphage | P1 |
| Coliphage | P2 |
| Coliphage | N15 |
| Bacteriophage | T3 |
| Bacteriophage | T4 |
| Bacteriophage | T7 |
| Bacteriophage | KU1 |

Bacteriophages of *Salmonella* spp

| | |
|---|---|
| Bacteriophage | Felix |
| Bacteriophage | P22 |
| Bacteriophage | L |
| Bacteriophage | 102 |
| Bacteriophage | 31 |
| Bacteriophage | F0 |
| Bacteriophage | 14 |
| Bacteriophage | 163 |
| Bacteriophage | 175 |
| Bacteriophage | Vir |
| Bacteriophage | ViVI |
| Bacteriophage | 8 |
| Bacteriophage | 23 |
| Bacteriophage | 25 |
| Bacteriophage | 46 |
| Bacteriophage | E15 |
| Bacteriophage | E34 |
| Bacteriophage | 9B |

Bacteriophages of *Shigella dysenteriae*

| | |
|---|---|
| Bacteriophage | ϕ80 |
| Bacteriophage | P2 |
| Bacteriophage | 2 |
| Bacteriophage | 37 |
| Bacteriophage | fs-2 |
| Bacteriophage | 138 |
| Bacteriophage | 145 |
| Bacteriophage | 149 |
| Bacteriophage | 163 |

Bacteriophages of *Vibrio cholerae*
Bacteriophages of *Mycoplasma arthritidis*

| | |
|---|---|
| Bacteriophage | MAV1 |

Bacteriophages of Streptococci

| | |
|---|---|
| Bacteriophage | CP-1 |
| Bacteriophage | ϕXz40 |
| Bacteriophage | 1A |
| Bacteriophage | 1B |
| Bacteriophage | 12/12 |
| Bacteriophage | 113 |
| Bacteriophage | 120 |
| Bacteriophage | 124 |

Bacteriophages of *Pseudomonas aeruginosa*

| | |
|---|---|
| Bacteriophage | D3 |
| Bacteriophage | ϕCTX |
| Bacteriophage | PP7 |

Bacteriophages of *Haemophilus influenzae*

| | |
|---|---|
| Bacteriophage | S2 |
| Bacteriophage | HP1 |
| Bacteriophage | flu |
| Bacteriophage | Mu |

Bacteriophages of *Staphylococcus aureus*

| | |
|---|---|
| Bacteriophage | Twort |
| Bacteriophage | tIII-29S |

-continued

| | |
|---|---|
| Bacteriophage | ϕPVL |
| Bacteriophage | ϕPV83 |
| Bacteriophage | ϕ11 |
| Bacteriophage | ϕ12 |
| Bacteriophage | ϕ13 |
| Bacteriophage | ϕ42 |
| Bacteriophage | ϕ812 |
| Bacteriophage | K |
| Bacteriophage | P3 |
| Bacteriophage | P14 |
| Bacteriophage | UC18 |
| Bacteriophage | 15 |
| Bacteriophage | 17 |
| Bacteriophage | 29 |
| Bacteriophage | 42d |
| Bacteriophage | 47 |
| Bacteriophage | 52 |
| Bacteriophage | 53 |
| Bacteriophage | 79 |
| Bacteriophage | 80 |
| Bacteriophage | 81 |
| Bacteriophage | 83 |
| Bacteriophage | 85 |
| Bacteriophage | 93 |
| Bacteriophage | 95 |
| Bacteriophage | 187 |

Bacteriophages of *Chlamydia*

| | |
|---|---|
| Bacteriophage | ϕCPAR39 |

Mycobacteriophage

| | |
|---|---|
| Bacteriophage | L5 |
| Bacteriophage | LG |
| Bacteriophage | D29 |
| Bacteriophage | Rvl |
| Bacteriophage | Rv2 |
| Bacteriophage | DSGA |

Bacteriophages of *Listeria monocytogenes*

| | |
|---|---|
| Bacteriophage | A118 |
| Bacteriophage | 243 |
| Bacteriophage | A500 |
| Bacteriophage | A511 |
| Bacteriophage | 10 |
| Bacteriophage | 2685 |
| Bacteriophage | 12029 |
| Bacteriophage | 52 |
| Bacteriophage | 3274 |

Bacteriophages of *Klebsiella pneumoniae*

| | |
|---|---|
| Bacteriophage | 60 |
| Bacteriophage | 92 |

Bacteriophages of *Yersinia pestis*

| | |
|---|---|
| Bacteriophage | R |
| Bacteriophage | Y |
| Bacteriophage | P1 |

The invention claimed is:

1. A process for the production of a modified bacteriophage comprising growing a bacterial host comprising genetic material encoding a modified bacteriophage, wherein said modified bacteriophage is able to replicate in said bacterial host; causing the bacteriophage to replicate in the bacterial host; and harvesting the bacteriophage, wherein said modified bacteriophage includes an α/β small acid-soluble spore protein (SASP) gene encoding a SASP which is toxic to the bacterial host, wherein the SASP gene is inserted into a lysis gene of said bacteriophage, wherein the SASP gene is under the control of a constitutive bacterial promoter which is foreign to the bacteriophage and the SASP gene and wherein the phage comprises a single copy of the SASP gene linked to said constitutive bacterial promoter.

2. The process according to claim 1, wherein the SASP comprises *Bacillus megaterium* SASP-C.

3. The process according to claim 1, wherein said bacteriophage comprises a modified *Staphylococcus aureus* bacteriophage.

4. The process according to claim 3, wherein the *Staphylococcus aureus* bacteriophage is a ϕ11 bacteriophage.

5. The process according to claim 1, wherein the promoter is selected from pdhA, rpsB, pgi, and fbaA.

6. The process according to claim 5, wherein the bacterial fbaA promoter is from *S. aureus.*

7. The process according to claim 1, wherein said bacteriophage is non-lytic.

8. The process according to claim 7, wherein said bacteriophage is holin$^{-}$.

9. The process of claim 1, wherein said promoter drives production of toxic levels of SASP when present in multiple copies in a target bacterium.

10. The process according to claim 1, wherein said bacteriophage further comprises a non-antibiotic resistance marker.

11. The process according to claim 10, wherein the non-antibiotic resistance marker is a cadmium resistance marker.

12. The process of claim 1, further comprising admixing said modified bacteriophage with a carrier.

13. A process for the production of a modified bacteriophage comprising growing a bacterial host comprising genetic material encoding a modified bacteriophage, wherein said modified bacteriophage is able to replicate in said bacterial host; causing the bacteriophage to replicate in the bacterial host; and harvesting the bacteriophage, wherein said bacteriophage comprises a ϕ11 bacteriophage having a holin gene into which is inserted a gene encoding *Bacillus megaterium* SASP-C under the control of an fbaA constitutive promoter.

14. The process according to claim 13, wherein the bacterial fbaA promoter is from *S. aureus.*

15. The process according to claim 13, wherein said bacteriophage is non-lytic.

16. The process of claim 13, wherein said promoter drives production of toxic levels of SASP when present in multiple copies in a target bacterium and wherein the bacteriophage contains a single copy of the SASP gene functionally linked to said fbaA constitutive bacterial promoter.

17. The process according to claim 13, wherein said bacteriophage further comprises a non-antibiotic resistance marker.

18. The process according to claim 17, wherein the non-antibiotic resistance marker is a cadmium resistance marker.

19. The process of claim 13, further comprising admixing said modified bacteriophage with a carrier.

20. The process of claim 1, wherein the constitutive promoter is a bacterial promoter.

* * * * *

SEQUENCE LISTING

<160> NUMBER OF SEQ ID NOS: 10

<210> SEQ ID NO 1
<211> LENGTH: 30
<212> TYPE: DNA
<213> ORGANISM: Artificial Sequence
<220> FEATURE:
<223> OTHER INFORMATION: Primer B1001

<400> SEQUENCE: 1
aactgcaggt gtattgcaac agattggctc 30

<210> SEQ ID NO 2
<211> LENGTH: 28
<212> TYPE: DNA
<213> ORGANISM: Artificial Sequence
<220> FEATURE:
<223> OTHER INFORMATION: Primer B1002

<400> SEQUENCE: 2
gctctagact ttgctccctg cgtcgttg 28

<210> SEQ ID NO 3
<211> LENGTH: 24
<212> TYPE: DNA
<213> ORGANISM: Artificial Sequence
<220> FEATURE:
<223> OTHER INFORMATION: Primer B1003

<400> SEQUENCE: 3
cgggatccga ctaaaaatta gtcg 24

<210> SEQ ID NO 4
<211> LENGTH: 29
<212> TYPE: DNA
<213> ORGANISM: Artificial Sequence
<220> FEATURE:
<223> OTHER INFORMATION: Primer B1004

<400> SEQUENCE: 4
ggactagtga atgagtatca tcatggagg 29

<210> SEQ ID NO 5
<211> LENGTH: 35
<212> TYPE: DNA
<213> ORGANISM: Artificial Sequence
<220> FEATURE:
<223> OTHER INFORMATION: Primer B1005

<400> SEQUENCE: 5
cgatggatcc tctcatttat aaggttaaat aattc 35

<210> SEQ ID NO 6
<211> LENGTH: 33
<212> TYPE: DNA
<213> ORGANISM: Artificial Sequence
<220> FEATURE:
<223> OTHER INFORMATION: Primer B1006

<400> SEQUENCE: 6
gcagaccgcg gctatttatc cttcactctc atc 33

<210> SEQ ID NO 7
<211> LENGTH: 34
<212> TYPE: DNA
<213> ORGANISM: Artificial Sequence -continued
<220> FEATURE:
<223> OTHER INFORMATION: Primer B1007

<400> SEQUENCE: 7
ctacggatcc tttatcctcc aatctactta taaa 34

<210> SEQ ID NO 8
<211> LENGTH: 29
<212> TYPE: DNA
<213> ORGANISM: Artificial Sequence
<220> FEATURE:
<223> OTHER INFORMATION: Primer B1008

<400> SEQUENCE: 8
catgccatgg aagttcctcc ttgagtgct 29

<210> SEQ ID NO 9
<211> LENGTH: 26
<212> TYPE: DNA
<213> ORGANISM: Artificial Sequence
<220> FEATURE:
<223> OTHER INFORMATION: Primer B1009

<400> SEQUENCE: 9
cgatccatgg caaattatca aaacgc 26

<210> SEQ ID NO 10
<211> LENGTH: 32
<212> TYPE: DNA
<213> ORGANISM: Artificial Sequence
<220> FEATURE:
<223> OTHER INFORMATION: Primer B1010

<400> SEQUENCE: 10
agtgagatct gaattcgctg attaaaagaa ac 32